(12) United States Patent
Kittelmann et al.

(10) Patent No.: US 7,982,169 B2
(45) Date of Patent: Jul. 19, 2011

(54) APPARATUS AND METHOD FOR DETECTING THE FOCAL POSITION OF AN OPTICAL SYSTEM AND OPTHALMOLOGICAL TREATMENT APPARATUS

(75) Inventors: Olaf Kittelmann, Berlin (DE); Peter Triebel, Jena (DE)

(73) Assignee: Wavelight AG, Erlangen (DE)

( * ) Notice: Subject to any disclaimer, the term of this patent is extended or adjusted under 35 U.S.C. 154(b) by 57 days.

(21) Appl. No.: 12/279,872

(22) PCT Filed: Feb. 20, 2007

(86) PCT No.: PCT/EP2007/001456
§ 371 (c)(1),
(2), (4) Date: Jan. 26, 2009

(87) PCT Pub. No.: WO2007/096136
PCT Pub. Date: Aug. 30, 2007

(65) Prior Publication Data
US 2009/0127429 A1    May 21, 2009

(30) Foreign Application Priority Data
Feb. 20, 2006   (DE) .......................... 10 2006 007 750

(51) Int. Cl.
G02B 7/04 (2006.01)
G01J 1/20 (2006.01)
G11B 7/00 (2006.01)
A61B 18/18 (2006.01)

(52) U.S. Cl. ............... 250/201.2; 250/201.5; 250/201.9; 369/112.01; 606/3

(58) Field of Classification Search .................. 250/216, 250/201.1–201.5, 201.8, 204, 559.05–559.08, 250/559.28, 559.29, 559.36, 201.9; 606/3–6; 351/205, 206, 246; 359/3, 17, 18, 30, 197, 359/234; 369/100, 109.01, 112.01–112.09, 369/119–122
See application file for complete search history.

(56) References Cited

U.S. PATENT DOCUMENTS
5,676,866 A    10/1997   in den Baumen et al.
5,818,592 A *  10/1998   Womack et al. .............. 356/511
(Continued)

FOREIGN PATENT DOCUMENTS
DE        10356415 A1    6/2005
(Continued)

OTHER PUBLICATIONS
International Patent Cooperation Treaty Patent Application PCT/EP2007/001456 International Search Report and Written Opinion of the International Searching Authority of Jun. 15, 2007.

*Primary Examiner* — Georgia Y Epps
*Assistant Examiner* — Don Williams
(74) *Attorney, Agent, or Firm* — Haynes and Boone, LLP

(57) ABSTRACT

An apparatus and a method are presented for detecting the focal position of an optical system (10) with a radiation source (12), a focusing imaging system (16), an at least partially reflective surface (18) on the focus (18a), a digital camera (24) for recording an image reflected by said surface (18), a computer (C) for evaluating the image recorded by the camera (24), and with an optical element (34; 36) in the beam path of the optical system (10) upstream of the focusing imaging system (16), which element influences said image depending on the focal position.

13 Claims, 4 Drawing Sheets

U.S. PATENT DOCUMENTS

| | | |
|---|---|---|
| 6,448,534 B1 | 9/2002 | Kobsa |
| 6,666,857 B2 | 12/2003 | Smith |
| 6,909,546 B2 | 6/2005 | Hirai |
| 7,207,983 B2 * | 4/2007 | Hahn et al. .................. 606/5 |
| 7,284,861 B2 * | 10/2007 | Fujieda .................. 351/206 |
| 2002/0171028 A1 | 11/2002 | Feldman |
| 2004/0021851 A1 | 2/2004 | Namiki |
| 2004/0051976 A1 | 3/2004 | Karin et al. |
| 2007/0010803 A1 | 1/2007 | Bischoff et al. |
| 2007/0179478 A1 | 8/2007 | Dobschal et al. |

FOREIGN PATENT DOCUMENTS

| | | |
|---|---|---|
| DE | 102004009212 A1 | 9/2005 |
| EP | 0627675 A1 | 12/1994 |
| EP | 1159986 A2 | 12/2001 |
| WO | 03/002008 A1 | 1/2003 |
| WO | 2005/039462 A1 | 5/2005 |

* cited by examiner

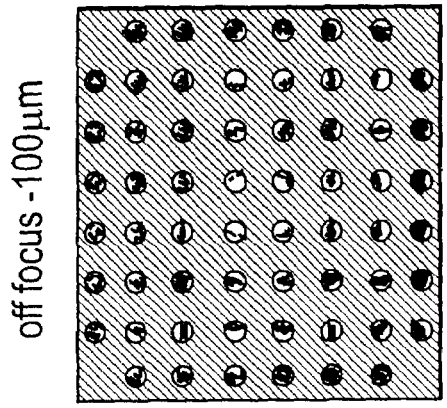
off focus -100μm
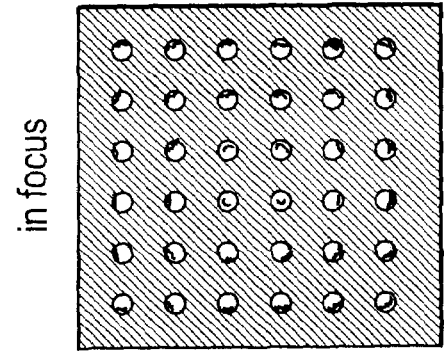
in focus
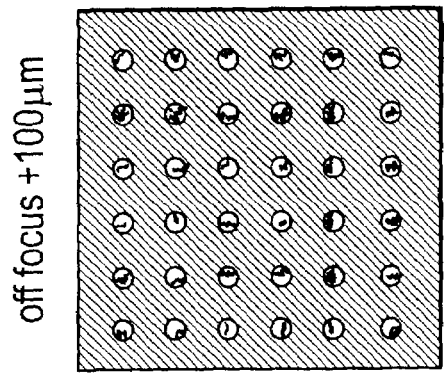
off focus +100μm
Fig. 5
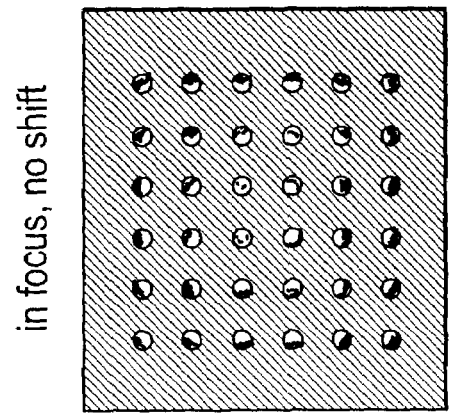
in focus, no shift
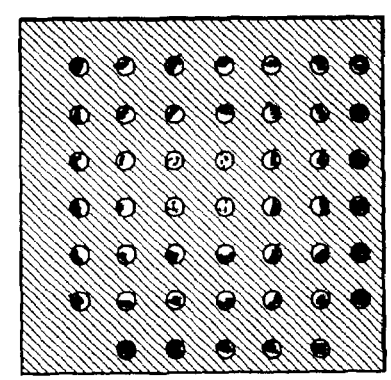
in focus -800μm lateral shift
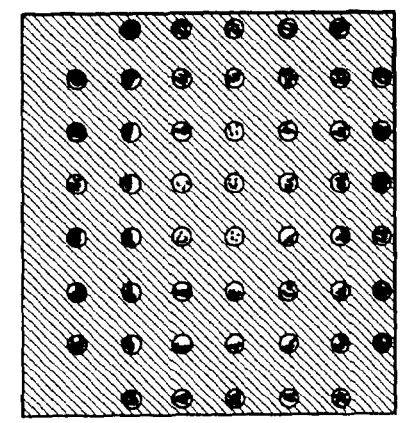
in focus -800μm lateral shift
Fig. 6

APPARATUS AND METHOD FOR DETECTING THE FOCAL POSITION OF AN OPTICAL SYSTEM AND OPTHALMOLOGICAL TREATMENT APPARATUS

This application was originally filed as Patent Cooperation Treaty Application Number PCT/EP2007/001456 filed Feb. 20, 2007, which claims priority of German Patent Application Number 102006007750.4, filed Feb. 20, 2006.

The invention relates to an apparatus and a method for detecting the focal position of an optical system. In particular, the invention relates to an apparatus and a method for detecting the depth of focus of an imaging optical system and moreover also to an apparatus and a method for controlling the focal position and in particular the depth of focus. Furthermore, the invention also relates to an opthalmological treatment and/or diagnosis apparatus using said apparatus and/or said method.

In the case of the optical systems under discussion here, the system in question is in particular an imaging optical system in a material processing installation using light sources, such as lasers and LEDs in particular. Material processing should be understood here to mean also material structuring in the microrange, e.g. for dielectric materials, such as biological tissue, or also metallic materials. In particular, the invention can be used in opthalmological optical systems, especially in refractive corneal surgery, such as LASIK, for example. A particularly suitable application area for the present invention in this case is fs-LASIK, thus refractive corneal surgery using a femtosecond laser.

In the aforesaid optical imaging systems, achieving highly precise material processing operations depends inter alia on exact control of the focal position. "Focal position" is understood here above all to mean not only the location of the focus in the direction of the optical axis (so-called depth of focus), however, but more generally also the position and orientation of the focused radiation, thus e.g. an offset in relation to the ideal optical axis of the system or angularity of the actual axis of the optical radiation in relation to the ideal (desired) optical axis. In fs-LASIK it is particularly important to adhere to the calculated depth of focus and this is a particular application of the present invention.

In DE 10 2004 009 212 A1, an optical contact element for laser material processing is presented. This contact element is used in the preferred embodiment for fs-LASIK. In this case this contact element consists of a diffractive optical structure. These structures are intended to minimize the incidence angles occurring due to high numerical apertures of the lens. The diffractive optical element (DOE) consists here of a grating structure with radially adjusted grating period. The grating periods in this case are between 200 l/mm and 500 l/mm. Values in the µm range are indicated as spot sizes. Due to optical limits, only one numerical aperture of approx. 0.3 is possible. Enlargement of the aperture is achieved by using a second diffractive element in the beam path of the lens. This DOE is likewise executed as a circular grating structure with a grating period that becomes larger towards the optical axis. Achieving higher numerical apertures is indicated here as an advantage of this execution. Furthermore, the contact element is executed curved. The radius of curvature corresponds to the radius of curvature of the eye, approx. 8 mm. Material processing is carried out with this uniformly preset radius of curvature. The suction attachment is carried out similar to WO 03/002008 A1 and EP 1 159 986 A2. Focus control is not carried out with this presented method.

In EP 0 627 675 A1, a diffractive optical device is presented for the mapping of one or more space points from a beam. Here the diffractive structure likewise consists of a segment-like arrangement of arbitrary binary or multistage diffractive elements. The arrangement can be a hexagonal or hexangular arrangement in particular. Thus mapping of a light beam is achieved. However, only an intensity or/and phase transformation is undertaken.

In US 2002/0171028, an apparatus for focus control is described. Here the returning light is brought by an imaging beam path to interference with a second bundle of rays and thus interferometric wave control is carried out.

Focus control by means of interferometric wavefront control is carried out likewise in U.S. Pat. No. 6,666,857 B2. The active wavefront control during the photoablation process on the human eye is then achieved by a combination of adaptive mirrors. No active wavefront control is to be undertaken.

In US 2004/0051976 A1, an optical arrangement of a confocal microscope, consisting of a laser source emitting predominantly in the UV spectral range, a beam expander, a diffractive pinhole array and an objective lens is described. A diffractive pinhole array is not described in its exact embodiment. The increase in efficiency can be seen as one advantage of this technical embodiment, as amplitude pinhole arrays have a typical transmission of between 4% and 10% depending on the aperture ratio. With a diffractive pinhole array, on the other hand, transmission values of such an optical element of up to 80% are possible, dependence on the aperture ratio or the number of pinholes only being conditional on the manufacturing here.

In US 2004/0021851, an optical arrangement consisting of a laser and subsequent beam shaping optics is used to measure the focal length of an unknown lens. Measurement of the focal length is carried out in this case by focusing on a reference surface at various distances. The portion of the radiation that is reflected back is detected. The spot diameters are then evaluated at the respective distances. The focal length is determined by means of the "Newton's" relation $Z\ Z'=f^2$. An optical grating, which is not described in greater detail, is used to decouple the portion of the radiation reflected back. The Jones matrix formalism is likewise drawn on to calculate the focal length. The accuracy of the method is near 1%.

In U.S. Pat. No. 6,909,546 B2, an optical arrangement consisting of a light source (Nd:YAG2w) and subsequent beam shaping optics is described. In this case two diffractive optical elements are used to homogenize the laser radiation. The first of the two DOEs is used here for homogenization and spatial frequency filtering. A subsequent pinhole carries out the spatial frequency filtering. Located inside the 2f system of spatial frequency filtering is the second DOE, which produces the desired intensity distribution in the far field. The far field is produced either by the field lens or by the $2^{nd}$ DOE. The desired intensity distribution is produced in the focus. Focus control is not carried out in this method.

SUMMARY

The object of the invention accordingly is to provide an apparatus and a method with which the focal position of an optical system can be determined precisely.

To this end the invention provides an apparatus for detecting the focal position of an optical system with a radiation source, a focusing imaging system, an at least partially reflective surface on the focus, a suitable digital sensor system (e.g. CCD camera, CMOS camera or the like) for recording an image that is reflected by said surface, a computer for evaluating the image recorded by the camera, and an optical element in the beam path of the optical system upstream of the focusing image system, which optical element influences said image depending on the focal position.

In this case said focusing optical imaging system is preferably focusing optics with adjustable (variable) focal position, thus in particular a system with which the location of the focus is adjustable in a direction parallel to the optical axis of the image (thus the depth of focus). In addition, in such a system the focal position is usually also adjustable in a direction perpendicular to the optical axis of the radiation, e.g. in fs-LASIK.

The apparatus according to the invention and the corresponding method thus serve in particular for the initial setting and alignment of an optical system such that immediately prior to material processing in relation to a predetermined plane, the so-called surface, the focus is adjusted precisely, in particular so that it lies exactly on this surface. When used in LASIK, said null plane is preferably a surface that arises due to the fact that the cornea is attached by suction in the area of interest to a reference surface (this is known as such to the LASIK expert). The flattening disc, which is transparent for the radiation used, is coated on its side facing the cornea and lying close to this such that a small percentage of the incident radiation is reflected. This reflection then produces said image of the radiation focused onto this null plane, which image is measured using said camera and evaluated. In ideal focusing, the focus should therefore lie exactly on this null plane (thus essentially on the flattened cornea surface in the example shown) and according to the evaluation of the reflected image the optical system is then adjusted so that the focusing is optimal, thus the position of the focus is exactly in this null plane. The optical system is thus set and aligned and can be used for the subsequent material processing. In the subsequent material processing the position of the focus is usually changed in relation to said null plane. Thus in fs-LASIK, for example, when cutting the so-called flap the focus is placed in the stroma and the focus positions are varied successively at right angles to the optical axis to produce the flap. This is known as such. The initial setting of the system as described above guarantees exact positioning of the foci at the desired target points.

In other material processing operations the null plane, which can also be described as the reference plane, can be defined differently and does not necessarily have to coincide with the surface of the material to be processed. The radiation focused onto the null plane and the measurement of the image reflected in this plane supply calibration of the optical system such that the setting of the optical imaging properties of the optical system for the ideal state of focusing exactly in the null plane is known due to the image measurement, so that then, starting out from these settings of the optical system, the focal position can be changed according to the desired material processing, e.g. into the inside of the cornea.

According to one configuration, said optical element, which influences the focus image to be measured depending on the focal position, is a diaphragm matrix (so-called pinhole array).

The optical element can also be a so-called diffractive optical element (DOE), which produces a dot pattern in the far field distribution (known as such to the person skilled in the art and not explained in greater detail here).

Said optical element can be arranged in the beam path of the reflected image between the reflective surface and the camera, or also outside this beam path. Advantages result in each case according to the type of application.

The amplitude (intensity) or the phase (wavefront) of the reflected image can preferably be influenced locally with the optical element and the defocus portions of the wavefront can be rendered visible.

It is also possible to provide said optical element in the beam path both phase-sensitively and amplitude-sensitively, in particular a combination thereof.

According to a preferred configuration, the optical element produces a dot pattern, in particular a regular dot pattern in the form of a matrix.

The invention also provides a method for detecting the focal position of an optical system, in which the radiation of a radiation source is mapped via a focusing imaging system in a focal plane and wherein to determine the focal position of the optical system including the imaging system an image is produced on the focus, which image is reflected there and is recorded by a camera, wherein an optical element influences the recorded image depending on the focusing of the radiation, and depending on said influencing of the image, information about the focal position of the focused radiation at the envisaged focal point is derived.

BRIEF DESCRIPTION OF THE DRAWINGS

Practical examples of the invention are described in greater detail below with reference to the drawing.

FIGS. 5, 6 show practical examples of images recorded by a camera with focusing mapping in the manner of a hole matrix with exact focusing and/or focusing errors.

DETAILED DESCRIPTION

Figure 1:
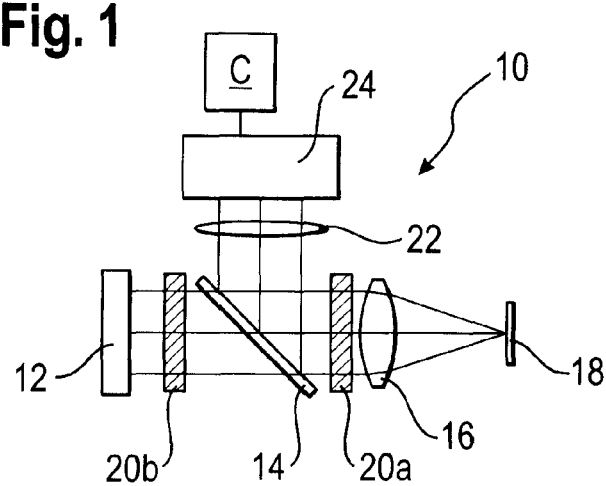
FIG. 1 shows schematically a first practical example of an optical system with an apparatus for detecting a focal position.

According to FIG. 1, an optical system 10 has a light source 12, which can be e.g. a laser (such as an fs-laser, for example) or an LED etc. The radiation emitted by the light source 12 passes through an output mirror 14 and is focused via a focusing imaging system 16 onto a plane 18. The focusing imaging system 16 is only indicated schematically in the figures by a single lens. Normally the focusing imaging system 16 has a plurality of lenses, of which one or more can be actuated for setting and changing the focus. Such optical imaging systems are known as such.

In FIG. 1, areas (points) are marked by the reference signs 20a and 20b at which an optical element described in greater detail below is optionally to be positioned. Examples of such optical elements are the optical elements 34 and 36 shown in FIGS. 3 and 4.

Radiation reflected by the reflective surface 18 passes via the optical imaging system 16 and if applicable the optical element arranged in area 20a and described in further detail below to the output mirror 14 and is deflected upwards from there in FIG. 1 via imaging optics 22 to a digital camera 24, e.g. a so-called CCD camera with high local resolution. The digital image recorded by the camera 24 is entered into a computer C and evaluated there, as described in greater detail further below.

Figure 2:
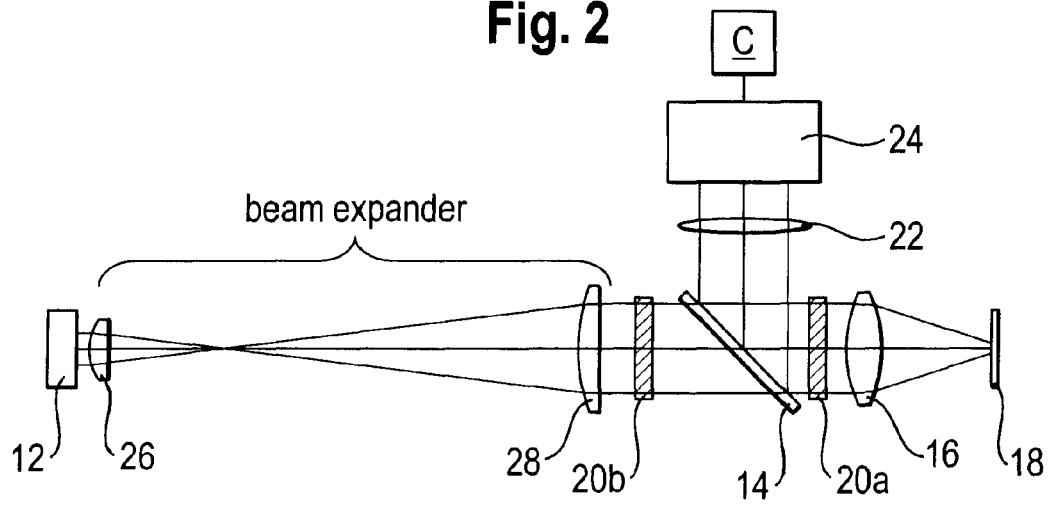
FIG. 2 shows a second practical example of an optical system with an apparatus for detecting the focal position.

FIG. 2 shows a modified practical example, with components and features having the same or similar functions being provided with the same reference signs. In the example according to FIG. 2, a beam expander (telescope) consisting of the optical elements 26, 28 is provided to expand the beam prior to its focusing with the imaging system 16. Instead of the Keppler telescope shown in the figure, another beam shaping system can also be used in its place. Generally the optical system designated a "beam expander" in FIG. 2 can also be a beam shaping system.

As already mentioned above, an optical element can be arranged in the areas 20a and/or 20b according to FIGS. 1 and 2 that, depending on the more or less optimal focusing by means of the imaging system 16 onto the reflective surface 18, influences the image described above, which was produced by reflection and recorded by the camera 24, and so facilitates a conclusion as to whether the focusing onto the plane corresponding to the surface 18 is precisely that which is desired or whether the focal position is displaced in relation to this plane, e.g. lies too far forward or too far back in the direction of the optical axis (so-called depth of focus).

Figure 3:
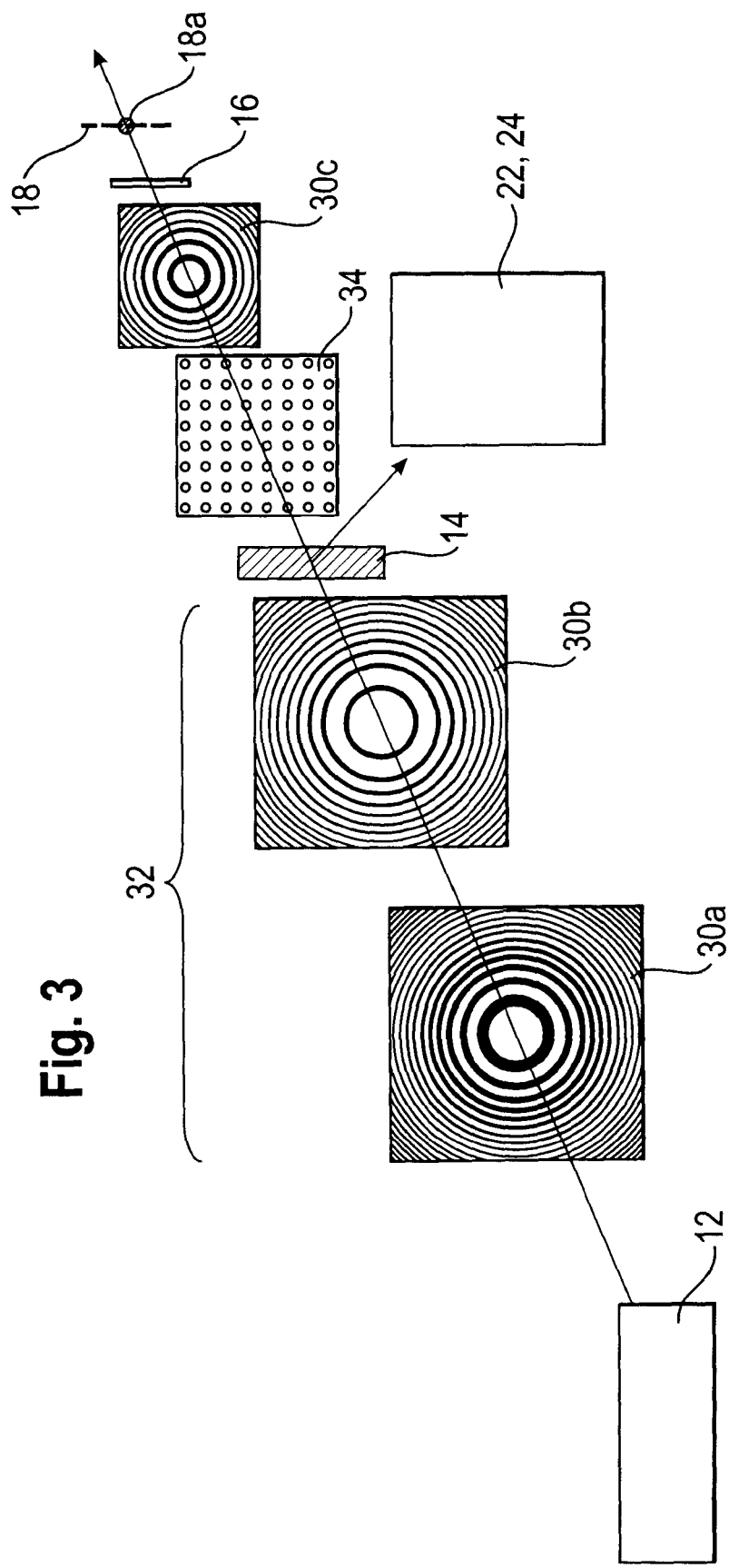
FIG. 3 shows schematically a practical example of an arrangement according to FIG. 2 with schematic representation of phase distributions of the radiation in the system and with a hole matrix.

According to FIG. 3, a shadow mask 34 is arranged as an optical element in the present sense in the beam path upstream of the focusing imaging system 16.

In the ideal case, the optical imaging system 16 is thus set such that the radiation coming from the light source 12 is focused precisely in the plane 18 at a predetermined point. The focus is marked in FIG. 3 by the reference sign 18a. The practical example according to FIG. 3 corresponds to the example according to FIG. 2 with a beam expander in the area indicated by reference sign 32. The phase distributions are also marked symbolically there by reference signs 30a, 30b, 30c.

The optical element 34 is a hole matrix with N×M individual holes in the regular arrangement shown. The optical element can be executed in this practical example as a pure amplitude-related element, thus influencing intensities of the radiation. Typical hole diameters in the shadow mask lie between 1 µm and 100 µm. The holes can be in particular hexangular, square, hexagonal or also circular. The arrangement of the individual holes is oriented to the beam profile used and the requirements in respect of accuracy with regard to the focal position. With the system described, focal positions can be determined accurate to a few µm. Since the radiation on the path to the plane 18 and the image reflected in the plane 18 each pass through the optical element 34, the image measured by the camera 24 is influenced depending on the accuracy of the focusing in the plane 18. A change in the focal position in relation to the plane 18 (which is the null plane defined above) of a few micrometers can be detected by evaluation of the image recorded by the camera 24 in the computer C.

It is also possible to determine the radiation output occurring in the focus by integration of the intensities measured by the camera 24 at the individual image points.

FIG. 5 shows, by way of example and schematically, reflection images obtained and evaluated in this manner. In this case FIG. 5 shows in the middle the matrix-like hole image obtained in the event that the optical system including the focusing imaging system 16 is set such that the focusing lies exactly on the desired point in the null plane 18. As stated, the reflective surface for producing the measured image also lies in this plane 18. As the hole image in FIG. 5, middle, shows, in the reflected image the individual holes are illuminated entirely homogeneously without a spherical portion, according to the input beam profile.

In the left-hand hole image, FIG. 5 shows a displacement of the focal position backwards by approx. 100 µm in relation to the null plane 18. Compared with exact focusing (FIG. 5, middle), the image evaluation yields a modification of the individual image dots in the matrix and the computer C is calibrated for the evaluation such that it "recognizes" this deviation. The calibration of the computer can take place e.g. experimentally in such a way that using a known optical imaging system changes in the reflected image produced are recorded and stored specifically depending on the focal position, so that then the focal position can be determined by comparison with actually measured images.

On the right, FIG. 5 shows defocusing by −100 µm with a lens focal length of 50 mm with corresponding modification of the hole image compared with ideal focusing. Generally speaking, the asymmetry of the image, as shown to the left and right in FIG. 5, permits analysis of the focusing. If, on the basis of image evaluation using the computer C, this analysis results in an asymmetrical brightness distribution in the image, then elements of the focusing imaging system 16 can be changed until the image evaluation shows that the focus lies exactly in the plane 18.

Figure 4:
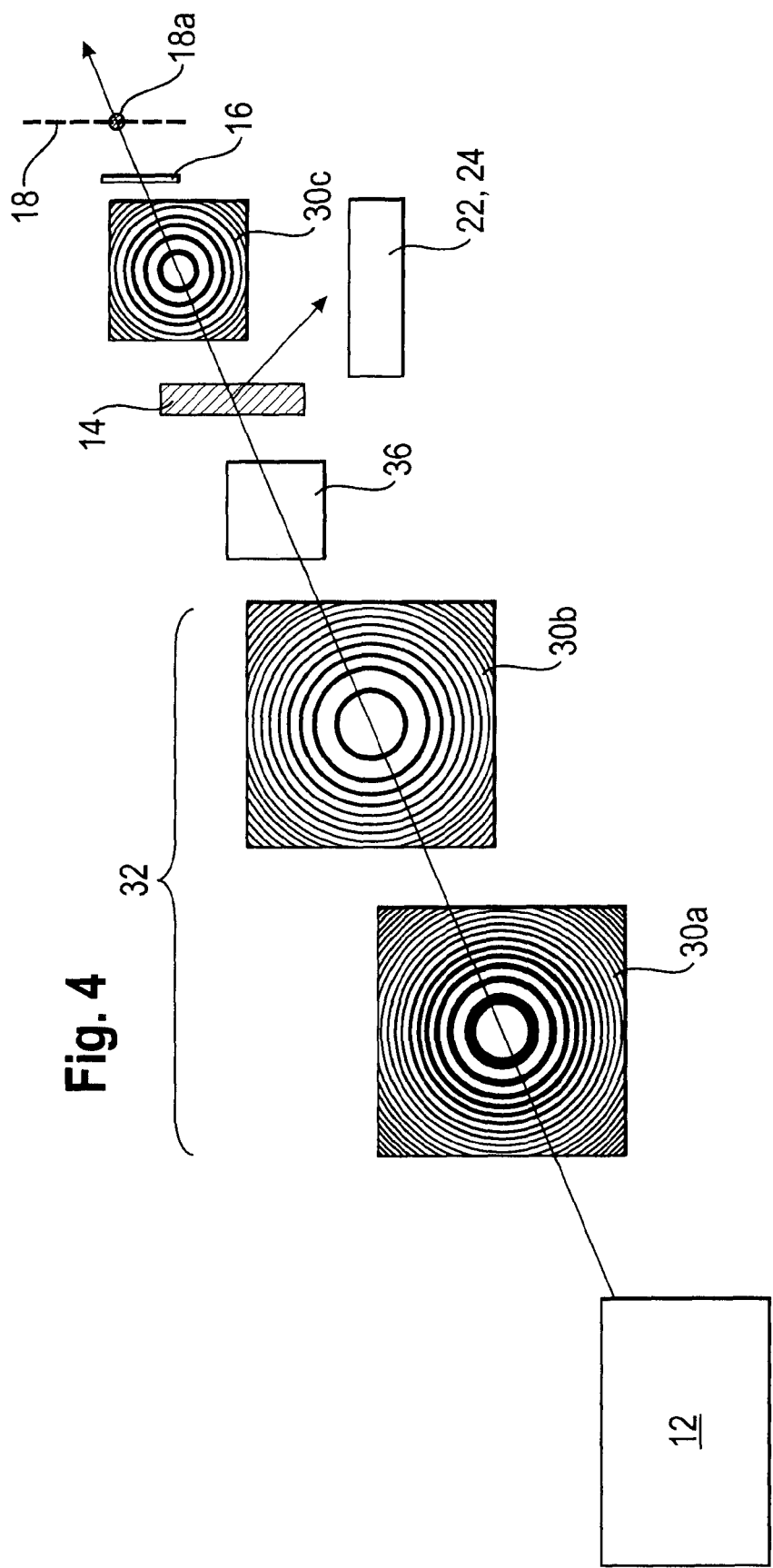
FIG. 4 shows a practical example of an arrangement according to FIG. 2 with a diffractive optical element.

FIG. 4 shows a practical example of the apparatus for detecting the focal position of an optical system 10, in which the optical element is arranged in area 20b in the practical example according to FIG. 2, thus in such a way that the image reflected on the plane 18 does not pass through the optical element 36 on its way to the camera 24.

The optical element 36 in this case is a diffractive optical element (DOE), which forms e.g. a "1 to N" beam splitter, thus splits an incident single beam into N single beams, wherein N can vary e.g. between 2 and 50. The divergence caused by the diffractive element 36 can be corrected refractively or diffractively by a second structure (not shown). Several diffractive optical elements can also be arranged one behind another, depending on the beam profile and desired analysis. An advantage of an arrangement with diffractive optical elements is the possibility of correction of the incident phase distribution. The phase distribution can be influenced by both the light source and the following optical elements, thus in particular the beam expander. In this practical example also, analogous to the description with reference to FIG. 3, the image reflected in the plane 18 is recorded by the camera 24 and evaluated in the computer C. FIG. 6 shows three images recorded by the camera 24 in the event that the diffractive optical element produces a matrix-like radiation distribution, wherein the image on the right in FIG. 6 shows the case of ideal focusing with relatively uniform illumination of the individual image dots. In FIG. 6, left, the case is shown in which the focal position deviates laterally from the ideal imaging point 18a, to be precise by several hundred micrometers. The individual image dots are illuminated asymmetrically. FIG. 6, middle, shows a focal position displaced laterally in another direction, wherein the individual matrix-like light dots are likewise illuminated less symmetrically than in the case of ideal focusing according to the image in FIG. 6, right.

An optical element 36 in the form of a DOE has the advantage compared with a hole matrix of high transmission. With a diffractive element, efficiency of between 80 and 90% can typically be achieved. Such an arrangement also facilitates very high dynamics in the evaluation of the focal position, i.e. deviations of the focus from the ideal target position can be established over a wide range.

It is also possible to arrange the diffractive optical element 36 in the areas 20a according to FIGS. 1 and 2.

The diffractive optical element can also be executed as a binary element or also as a so-called multi-level grating structure. The grating structures can be one-dimensional or also two-dimensional.

If an arrangement according to FIG. 1, 2, 3 or 4 is used in fs-LASIK, then the reflective surface 18, which defines the null plane explained above, can be e.g. the rear of a transparent disc in a suction apparatus known as such, which is constructed (coated or uncoated) such that a small percentage of the incident radiation is reflected to obtain the image to be recorded by the camera 24.

The following are used in particular as diffractive optical elements: gratings, Fresnel zone lenses, so-called beam-shaping elements etc. So-called refractive optical components can also be used as element (36): e.g. micro-lens arrays, beam-shaping elements etc. If the optical element 34 is used for amplitude analysis, then shadow masks or also arrangements of holes in any geometry such as square, hexangular, hexagonal etc. are particularly suitable, depending on the beam type and analysis aim.

The optical element can also be formed as a slot or as an arrangement of several slots.

Using the arrangements described, not only can the focal position be determined and controlled, but beam divergences, laser outputs, deviations of the radiation from the optical axis, deviations in the so-called beam product $M^2$ or changes in the output beam profile of the light source 12 can also be detected, since all these beam parameters can have an influence on the reflected image recorded by the camera 24. With regard to all these beam parameters the computer C can be provided experimentally beforehand with a database through targeted trials, which database assigns deviations from the ideal target values, each of which correspond to image alterations, to individual beam parameters, so that the system is adjustable to ideal values by intervention with corresponding correcting variables. The use of diffractive optical elements here facilitates compensation of any phase alterations possibly occurring in the beam path that can also influence the focal position. The Hartmann Shack sensor, known as such, does not facilitate such an analysis.

The invention claimed is:

1. Apparatus for detecting the focal position of an optical system, said apparatus comprising:
   a radiation source for producing radiation,
   a focusing imaging system,
   a disc which is substantially transparent to the radiation but includes a partially reflective surface that reflects a small percentage of the radiation incident on said disc,
   a digital sensor system for recording an image reflected by said surface,
   a computer for evaluating the image recorded by the digital sensor system, and
   an optical element in the beam path of the optical system upstream of the focusing imaging system, wherein the optical system is a LASIK arrangement and the optical element in the beam path influences the phase or amplitude of said image depending on the focal position and wherein the partially reflective surface reflects a small percentage of the incident radiation to obtain the image to be recorded using the digital sensor system.

2. Apparatus according to claim 1, characterized in that the optical element is a hole matrix.

3. Apparatus according to claim 1, characterized in that the optical element is a diffractive optical element.

4. Apparatus according to claim 3, characterized in that the diffractive optical element produces a dot pattern, in particular a dot pattern in the form of a matrix.

5. Apparatus according to one of the preceding claims, characterized in that the optical element is arranged in the beam path of said reflected image.

6. Apparatus according to one of claims 1 to 3, characterized in that the optical element is arranged outside the beam path of the reflected image.

7. Apparatus according to claim 1, characterized in that the optical element has a grating structure.

8. Apparatus according to claim 1, characterized in that the radiation source is an fs-laser.

9. Apparatus according to claim 1 with means for setting the imaging of the optical system depending on the evaluation of the computer.

10. Method for detecting the focal position of an optical system immediately prior to material processing, in which the radiation of a radiation source is mapped via a focusing imaging system in a focal plane and wherein to determine the focal position of an optical system including the imaging system by means of an optical element in the beam path of an image is produced on the focus, which is reflected from a surface of a disc positioned adjacent a cornea and is recorded by a camera, wherein said optical element influences the image recorded depending on the focusing of the radiation and wherein depending on said influencing of the image a conclusion is derived about the focal position of the focused radiation in relation to an envisaged focal point characterized in that by means of the optical element the phase or amplitude of the image is influenced depending on the focal position and that the optical system is a LASIK arrangement, wherein the partially reflective surface reflects a small percentage of the incident radiation to obtain the image to be recorded using the digital sensor system.

11. Method according to claim 10, wherein by means of said derived conclusion about the focal position an optical element of the optical system is set to change the focal position.

12. Apparatus for detecting the focal position of an optical system, the apparatus comprising:
   a radiation source,
   a focusing imaging system that receives radiation from said radiation source and generates a beam having a path and a focus;
   a flattening disc having a coating defining an at least partially reflective surface at the focus,
   a digital sensor system for recording an image reflected by said surface and providing a signal corresponding to the image sensed by the digital sensor system,
   a computer connected to said digital sensor system and receiving said corresponding signal, said computer evaluating the signal corresponding to the image sensed by the digital sensor system, and
   an optical element in the beam path of the optical system upstream of the focusing imaging system, wherein the optical element in the beam path influences the phase or amplitude of said image depending on the focal position, wherein the partially reflective surface reflects a small percentage of the incident radiation to obtain the image to be recorded using the digital sensor system.

13. The apparatus of claim 12, wherein the radiation source is a femto-second laser.

* * * * *